(12) United States Patent
Livne et al.

(10) Patent No.: US 8,317,701 B2
(45) Date of Patent: Nov. 27, 2012

(54) DEVICE AND METHOD FOR INTRA-OCULAR PRESSURE MEASUREMENT

(75) Inventors: Abraham Livne, Kfar Saba (IL); Ilan Ron, Kfar Saba (IL)

(73) Assignee: A.T.I.- Advanced Medical Technologies Ltd., Hod Hasharon, IL (US)

( * ) Notice: Subject to any disclaimer, the term of this patent is extended or adjusted under 35 U.S.C. 154(b) by 0 days.

(21) Appl. No.: 11/816,449

(22) PCT Filed: Feb. 16, 2006

(86) PCT No.: PCT/IL2006/000202
§ 371 (c)(1),
(2), (4) Date: Aug. 16, 2007

(87) PCT Pub. No.: WO2006/087715
PCT Pub. Date: Aug. 24, 2006

(65) Prior Publication Data
US 2008/0154114 A1    Jun. 26, 2008

(30) Foreign Application Priority Data
Feb. 17, 2005    (IL) .......................................... 166962

(51) Int. Cl.
*A61B 3/16* (2006.01)
(52) U.S. Cl. ......... 600/405; 600/398; 600/399; 600/561
(58) Field of Classification Search .......... 600/398–406, 600/489, 504, 558, 561
See application file for complete search history.

(56) References Cited

U.S. PATENT DOCUMENTS

| | | | |
|---|---|---|---|
| 1,423,293 A * | 7/1922 | Amsler | 600/403 |
| 3,598,478 A | 8/1971 | Townsley | |
| 3,977,237 A * | 8/1976 | Tesi | 600/405 |
| 4,523,597 A | 6/1985 | Sawa et al. | |
| 4,547,668 A * | 10/1985 | Tsikos | 250/231.19 |
| 4,573,778 A | 3/1986 | Shapiro | |
| 4,636,078 A * | 1/1987 | Podvin | 356/450 |
| 4,724,843 A * | 2/1988 | Fisher | 600/401 |
| 4,834,070 A * | 5/1989 | Saitou | 600/108 |
| 5,032,020 A * | 7/1991 | Robert | 351/219 |
| 5,090,400 A * | 2/1992 | Saito | 600/108 |
| 5,197,473 A * | 3/1993 | Fedorov et al. | 600/398 |
| 5,349,955 A * | 9/1994 | Suzuki | 600/398 |

(Continued)

FOREIGN PATENT DOCUMENTS
JP    5056932    3/1993

*Primary Examiner* — Rene Towa
(74) *Attorney, Agent, or Firm* — Frommer Lawrence & Haug LLP; William S. Frommer

(57) ABSTRACT

A device and method are presented for use in non-invasive measurement of a patient's intra-ocular pressure (IOP). The device comprises a probe unit comprising a flexible membrane which is to be brought into contact with a patient's eyelid thereby enabling a contacting region of the membrane to match a shape of the eyelid defined by the shape of the patient's cornea. The device is configured to enable controllably varying application of force to the membrane against the eyelid and to enable illumination of the membrane at least within the contacting region thereof, the deformation of the illuminated membrane affecting detected light returned from the membrane, thereby enabling identification of a condition of applanation of a desired area of the membrane by identifying desired data indicative of the detected light and allowing the IOP measurement upon identifying said condition.

38 Claims, 10 Drawing Sheets

U.S. PATENT DOCUMENTS

| | | | |
|---|---|---|---|
| 5,546,941 A | 8/1996 | Zeimer et al. | |
| 5,836,873 A * | 11/1998 | Fresco | 600/398 |
| 5,868,580 A * | 2/1999 | Amrein et al. | 434/271 |
| 5,954,646 A * | 9/1999 | Jost et al. | 600/406 |
| 5,967,990 A * | 10/1999 | Thierman et al. | 600/459 |
| 6,083,160 A | 7/2000 | Lipman | |
| 6,110,110 A | 8/2000 | Dublin, Jr. et al. | |
| 6,361,495 B1 * | 3/2002 | Grolman | 600/401 |
| 6,440,070 B2 | 8/2002 | Israel | |
| 6,606,540 B1 | 8/2003 | Gross | |
| 6,941,813 B2 * | 9/2005 | Boukhny et al. | 73/705 |
| 2002/0193675 A1 | 12/2002 | Rathjen | |
| 2006/0189839 A1 | 8/2006 | Laniado et al. | |

\* cited by examiner

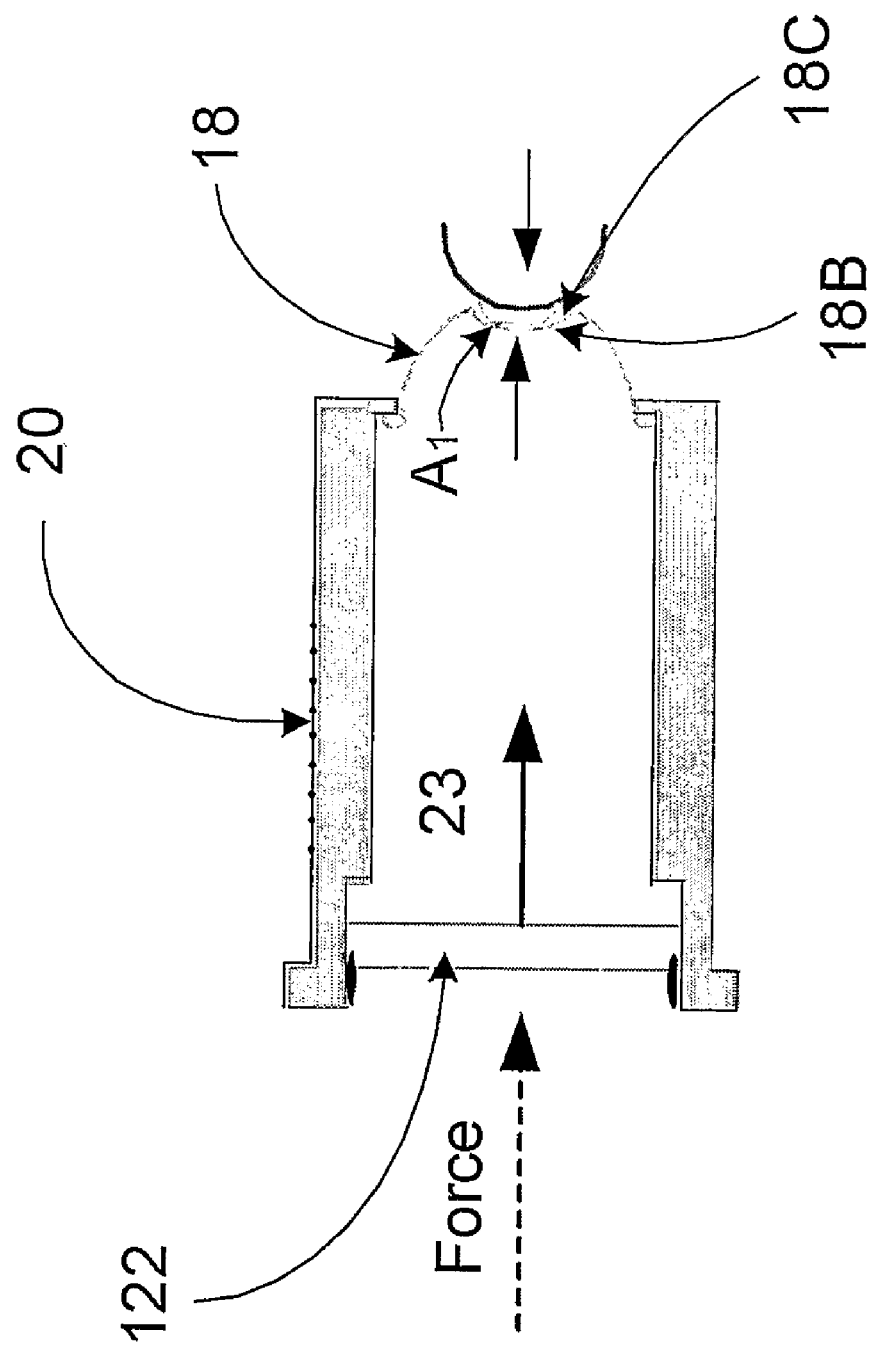

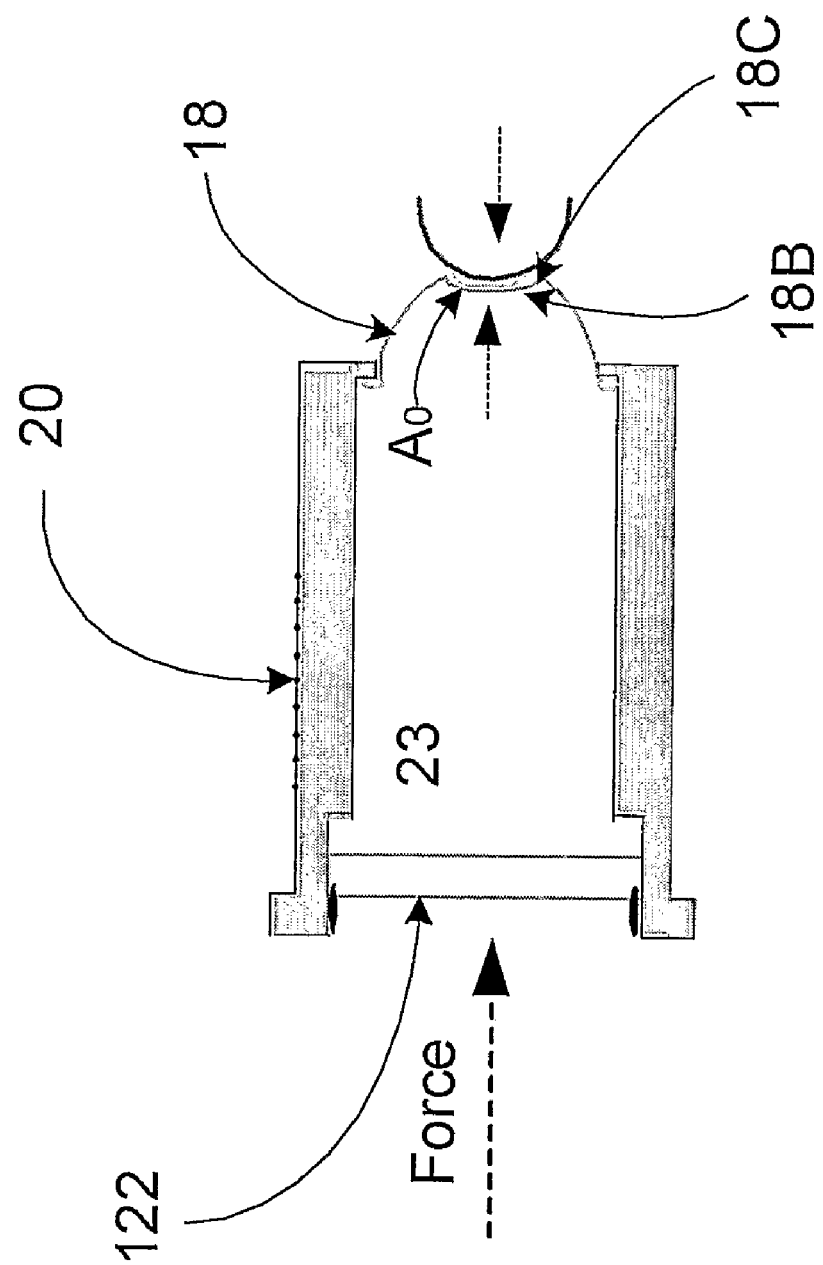

DEVICE AND METHOD FOR INTRA-OCULAR PRESSURE MEASUREMENT

FIELD OF THE INVENTION

This invention is generally in the field of medical devices, and relates to a device and method for non-invasive measurement of intra-ocular pressure (IOP).

BACKGROUND OF THE INVENTION

Various diagnostic procedures require IOP measurements, most widely used for diagnosing glaucoma condition, i.e., increase in IOP that can cause optic nerve degeneration which results in loss of vision. Conventional IOP measurement systems are based on the principles of a mechanical tonometer, namely a direct pressure measurement. Such tonometers are of contact and non-contact types. The contact type systems utilize a measuring probe directly pressed against a patient's eyeball, and measurement of a pressure corresponding to a given degree of deformation; in the non-contact measurement systems, a stream of air is blown onto the cornea surface, and a deformation of the cornea caused by this stream is measured.

JP 5056932 discloses a tonometer aimed at enabling a patient to measure his own intra-ocular pressure with ease at home, etc. The patient holds an outside cylinder of the tonometer device and presses a contact member to the eye to be examined in such a manner that this member comes into contact with the eye by crossing the eyelid. A spring which is contracted by a pressing force is used, and is associated with a sensor, such that light emitted from a light source is made incident on the sensor via a mirror, when the spring attains a prescribed value. This light acts as a signal to cause electromagnetic driving parts of the device to drive a press-fitting member, mounted coaxial with the contact member, toward the eye to be examined. The moving quantity of the press-fitting member of this time is detected by another light source and an array sensor, and the intra-ocular pressure is measured from the driving force and the moving quantity of the press-fitting member.

U.S. Pat. No. 5,349,955 discloses a tonometer adapted to measure intra-ocular pressure by applying pressure onto an eye being examined via its eyelid. The tonometer has a pressure means that presses against the eyelid of a subject eye to thereby apply pressure to the eye. The load applied to the pressure means is detected by a load sensor and used to calculate intra-ocular pressure of the eye. The tonometer is structurally simple and compact, operationally safe, and does not cause the patient to feel fear and discomfort.

U.S. Pat. No. 6,440,070 discloses an intra-ocular pressure measurement apparatus including a housing and a processor. The housing has a protuberance with a flat surface, and the processor includes a distance-measuring unit and a force-measuring unit. Intra-ocular pressure is calculated based on force/distance relationships, where the distance includes a measurement to an internal element of the eye. The processor calculates intra-ocular pressure by determining a zero displacement pressure.

The most widely used tonometers are based on the principles of the Goldmann Applanation Tonometer of direct pressure measurement following applanation of a cornea. According to the "Gold Standard", a flattened diameter optimal to this technique is chosen to define a flat contact surface such that no component of corneal tension is perpendicular to the cornea/tonometer interface.

SUMMARY OF THE INVENTION

There is a need in the art to facilitate IOP measurements, by providing a novel non-invasive measurement device and method.

The technique of the present invention provides for the IOP measurement on a closed eye via the eyelid. The device of the present invention can thus be easily used by a physician as well as by a patient himself at home, thus simplifying monitoring of the glaucoma condition. The device of the present invention has a simple and non-expensive configuration, and provides for quick and precise measurements.

The present invention is based on measuring a force applied to the cornea when a specific area of the cornea is desirably deformed (flattened, considering that IOP is equal to the force per flattened area). Accordingly, the measurement device is to provide information about the applied force and the flattened surface area of the cornea.

The IOP measurement that is to be taken is that corresponding to a condition when the flattened area is equal to the specific area considered in the relation between the applied force and IOP. Hence, an indication should be provided on the adjustment of the flattened area to a desired value. To this end, the present invention utilizes illumination of a surface region of a membrane and detection of light returned from the illuminated region of the membrane, which is brought into contact with the eyelid and is shifted (deformed) from its curved state into its flattened state under the applied force, thus causing a change in the detected light. The light returned from the membrane may be a light response of the membrane surface (reflection, for instance) and/or may be indicative of an image of the membrane. The latter is preferably acquired as an image of a certain pattern (such as concentric circles, or a grid) via the light returned from the membrane. This can be achieved by forming the membrane's surface with a pattern (e.g. imprinted) and/or projecting a certain pattern onto the membrane or passing light returned from the membrane through a certain pattern prior to being detected.

It should be understood that the term "membrane" used herein refers to a flexible surface, which when brought in contact with the patient's eyelid is deformable under a force applied thereto against the eyelid. The membrane may be a separate element, may be a surface of a distal end of a probe, may be a surface of an inflatable unit, etc.

Deformation of the membrane (under applied pressure) affects a change in the detected light. The flattened state (generally, desired deformation) of the membrane is identified by the detection of a predetermined light response of the illuminated region of the membrane (e.g. predetermined intensity of the detected light returned from the membrane) and/or a predetermined image of a certain pattern, and is thus indicative of the condition corresponding to that required for the IOP measurement.

It should be understood that imaging of a certain pattern can be achieved by carrying out at least one of the following: providing the pattern on the membrane surface, projecting the pattern onto the membrane, and passing light returned from the membrane through the pattern. Thus, in some embodiments of the invention, the detection of the desired membrane deformation can be achieved by image processing of a dedicated image imprinted or projected onto the inner surface of the membrane.

The device of the present invention thus includes a probe unit having a flexible membrane, which may or may not be carried by the probe housing. The flexible membrane can be curved (like a semi-sphere) to match the geometry of the external surface of the eyelid, and deforms when pressed against the eyelid (becomes flattened). The probe is preferably configured for both the application of force on the eye (e.g., using a force applying mechanism, e.g. specific pressurizing assembly; or not) and the measurement of the flattened area, but generally a separate measurement unit can be used. The device also includes mechanisms for measuring the flattened surface and the applied force, and preferably includes a mechanism preventing the extra force application to the eye.

There is thus provided according to one broad aspect of the invention, a device for use in non-invasive measurement of a patient's intra-ocular pressure (IOP), the device comprising: a probe unit having a flexible membrane which is to be brought into contact with a patient's eyelid thereby enabling a contacting region of the membrane to match a shape of the eyelid defined by the shape of the patient's cornea; the probe being configured to enable controllably varying application of force to the membrane against the eyelid and to enable illumination of the membrane at least within the contacting region thereof and detection of light returned from the illuminated membrane region, the deformation of the illuminated membrane affecting detected light returned from the membrane, thereby enabling identification of a condition of applanation of a desired area of the membrane by identifying desired data indicative of the detected light and allowing the IOP measurement upon identifying said condition.

According to some embodiments of the invention, the inner surface of the membrane, at least within the contacting region, is light responsive, e.g. is at least partially reflective to the certain light spectrum, or contains a fluorescent material providing a fluorescent response to a certain light spectrum. The membrane surface (reflective and/or fluorescent) may be formed with a certain pattern (grid).

According to some other embodiments of the invention, the inner surface of the membrane contains any type of a pattern, an image of which can be acquired by any type of imaging detector(s) (CCD camera, for instance), to be electronically processed. According to yet other possible configurations, a pattern is used either in the illumination or detection channel, the pattern image being detectable by a suitable pixel array detector.

Preferably, the probe has a hollow housing (e.g., of a cylindrical geometry) defining a space for light propagation towards and away from the membrane, and may contain an optical lens. The inner surface of the housing is preferably substantially non-reflective with respect to the light spectrum used in the device.

The device includes an optical system configured for directing light of the certain light spectrum towards the membrane and detecting light returned from the membrane (detecting reflection or obtaining an optical image). The optical system includes an illuminator unit and a light detection unit (e.g. sensor array). The configuration may be such that the light detection unit generates data indicative of the desired light detection, or the output of the detection unit is connected (via wires or wireless) to a control unit configured to analyze data indicative of the detected light and generate respective data.

The identification of the desired light detection can be implemented by making on a light sensitive surface of the detector unit a reference mark defining the detection of the desired light reflection, or by applying signal processing of the acquired data. According to another embodiment, the same can be implemented by using a single light detector element located in the optical path of the desired light reflection propagation (thus preventing detection of light corresponding to any other state of the membrane deformation), or an array of light detector elements.

The configuration may be such that a lighting element (light emitter of fiber) of the illuminator unit is accommodated at a central axis of the hollow housing and is configured to illuminate a substantially circular spot on the light responsive inner surface of the containing region of the membrane. The light detector unit may be configured to define the light sensitive surface (element) surrounding the lighting element. The reference mark (or light detecting element) may be in the form of an annular region of the light sensitive surface around the lighting element.

According to yet another embodiment, the illuminator may be configured with a certain pattern generator to thereby project the illuminating pattern onto the membrane. In this case, the detector unit is associated with an image processing utility for processing and analyzing an image formed by the detected light from the membrane.

The probe is also configured and operable to apply pressure to the membrane from the inner side thereof, to thereby cause the application of force against the eyelid when the membrane is brought into contact with the eyelid. As indicated above, this can be implemented providing a pressurizing mechanism in the probe or just configuring the probe to enable application of pressure by the entire probe movement towards the eyelid.

The pressurizing assembly may be configured as an air pump assembly. Such an air pump assembly may include a partition located across the housing being spaced from the distal end thereof, thereby defining a space between the partition and membrane. The partition, which is optically transparent, is formed with an air inlet associated with an air pump, and preferably also includes an air output associated with a pressure sensor to thereby measure a force applied from the eyelid to the membrane while the membrane is pressed against the eyelid by the air pressure.

The pressurizing assembly may include an optically transparent piston spaced from the membrane by a substantially non-compressible optically transparent liquid medium, and driven for reciprocating movement towards and away from the membrane.

The piston may be driven for the reciprocating movement by a helical spring or any other motorized motion control or force applying mechanism. The configuration may be such that incident light coming from the optical system and reflected light coming towards the optical system pass through the helical spring or any other motorized motion control or force applying mechanism.

The device also includes a measurement unit for measuring pressure applied to the membrane from the inner side thereof.

Preferably, the housing is configured so as to restrict the reciprocating movement of the piston to a certain distance to thereby prevent the applied force to exceed a predetermined value.

The device preferably includes an indication arrangement configured to generate an indication signal upon detecting the condition of applanation of the desired area of the membrane to thereby actuate calculation of the respective IOP value. The indication arrangement includes a signal generator configured to be responsive to data indicative of the desired light detection, the output of the signal generator being connectable (via wires or wireless) to a control unit preprogrammed to be responsive to the output indication signal and to the measured pressure to calculate the corresponding IOP value. The same control unit may include said image processing utility connectable to the light output of a light detector.

According to another broad aspect of the invention, there is provided a system for non-invasive measurement of a patient's intra-ocular pressure (IOP), the system comprising: a probe unit comprising a flexible membrane which is to be brought into contact with a patient's eyelid thereby enabling a contacting region of the membrane to match a shape of the eyelid defined by the shape of the patient's cornea; and an optical system configured to illuminate the membrane surface at least within the contacting region and detect light returned therefrom; the system being configured to enable controllably varying application of force to the membrane against the eyelid, a change in the detected light being indicative of the membrane deformation under application of force against the eyelid, the system thereby enabling identification of a condition of a predetermined deformation of a desired area of the membrane by identifying the predetermined light detection and allowing the IOP measurement upon identifying said condition.

According to yet another broad aspect of the invention, there is provided a method for use in non-invasive measurement of intra-ocular pressure (IOP), the method comprising: providing a flexible membrane, thereby allowing to bring the membrane by an outer surface thereof into contact with a patient's eyelid, applying controllably varying force to the membrane against the eyelid causing deformation of the contacting region of the membrane to match a shape of the eyelid defined by the shape of the patient's cornea, such that further deformation of the membrane causes applanation of the contacting region of the membrane, illuminating the membrane and detecting light returned therefrom, the detected light varying with the deformation of the membrane, thereby enabling identification of a condition of applanation of a desired area of said membrane by identifying a predetermined condition of the detected light from the membrane and allowing the IOP measurement upon identifying said condition.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 3A to 3D illustrate more specifically the deformation of a membrane under the application of pressure in the device of the present invention;

DETAILED DESCRIPTION OF THE INVENTION

Figure 1:
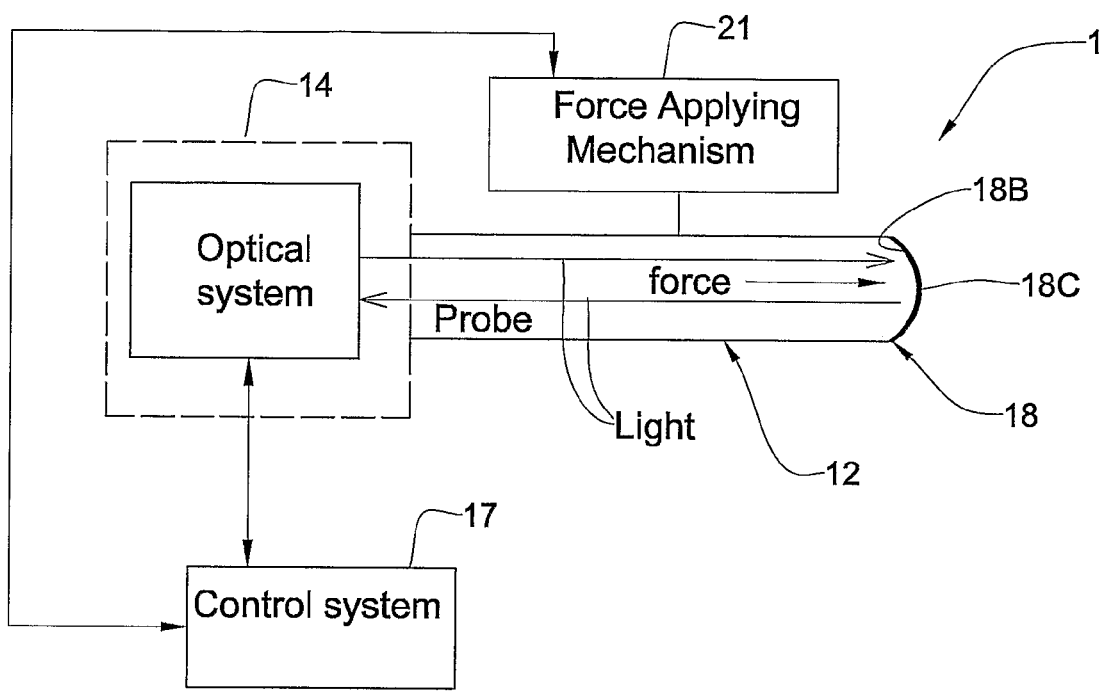
FIG. 1 is a block diagram of an example of a device of the present invention for use in IOP measurements.

Referring to FIG. 1, there is illustrated, by way of a block diagram, an example of a device 1 of the present invention. The device 1 is configured for use in non-invasive measurement of a patient's intra-ocular pressure (IOP). The device 1 includes a probe unit 12 having a flexible membrane 18 which is to be brought into contact with a patient's eyelid (not shown). In the example of FIG. 1, the membrane is carried by the distal end of the probe unit by which it is brought into contact with a patient's eyelid. However, it should be understood that the membrane may be a separate element. The probe 12 is configured to apply controllably varying pressure to the membrane against the eyelid thereby causing membrane deformation. To this end, a certain force applying mechanism 21 can be used, some examples of which are described further below. Generally, this may be any motion control mechanism, for either applying the force to the membrane only or displacing the entire probe (as shown in the figure in dashed lines) with the membrane towards the eyelid thus applying pressure and causing membrane deformation. Thus, the flexible membrane 18, when brought into contact with the eyelid, is deformable under application of force against the eyelid. When an inner surface 18B of the membrane 18 (at least with a contacting region 18C) is illuminated and light returned from the illuminated region is detected, the membrane deformation effects a change in the detected light.

The probe 12 is preferably configured to define a space (cavity) for input light propagation towards the inner surface of the membrane and for propagation of light returned from the membrane. The probe 12 is associated with an optical system 14 configured to direct the input light onto the membrane's surface 18B and detect the light returned thereof. It should be noted that the optical system may or may not be carried by the probe 12 (as shown in the figure in dashed lines). The optical system 14 may include a light source and/or a light detection unit as its constructional part(s), or may be configured as a light direction unit associated with external light source and/or detection unit. The output of the optical system 14 (its detector unit which is not shown here) as well as data indicative of the applied pressure is received and analyzed at a control system 17, thereby enabling identification of a condition of applanation of a desired area of the membrane by identifying a predetermined condition of the detected light and allowing the IOP measurement upon identifying said condition.

The membrane's surface 18B (at least within the contacting region 18C) may just be light responsive (e.g. may be light reflective surface, at least partially reflective, or may be fluorescent surface), in which case the predetermined condition of the detected light is determined by detecting the predetermined light intensity of the returned light.

The membrane's surface 18B may be imprinted with a certain pattern; and/or the optical system may be configured for imaging a certain pattern via the light returned from the membrane, e.g. utilizing projection of a pattern onto the membrane or passing light from the membrane through a pattern. In either one of these cases, the control system 17 is configured to carry out a suitable image processing to identify a predetermined condition (i.e. predetermined image) of the detected light.

Figure 2A:
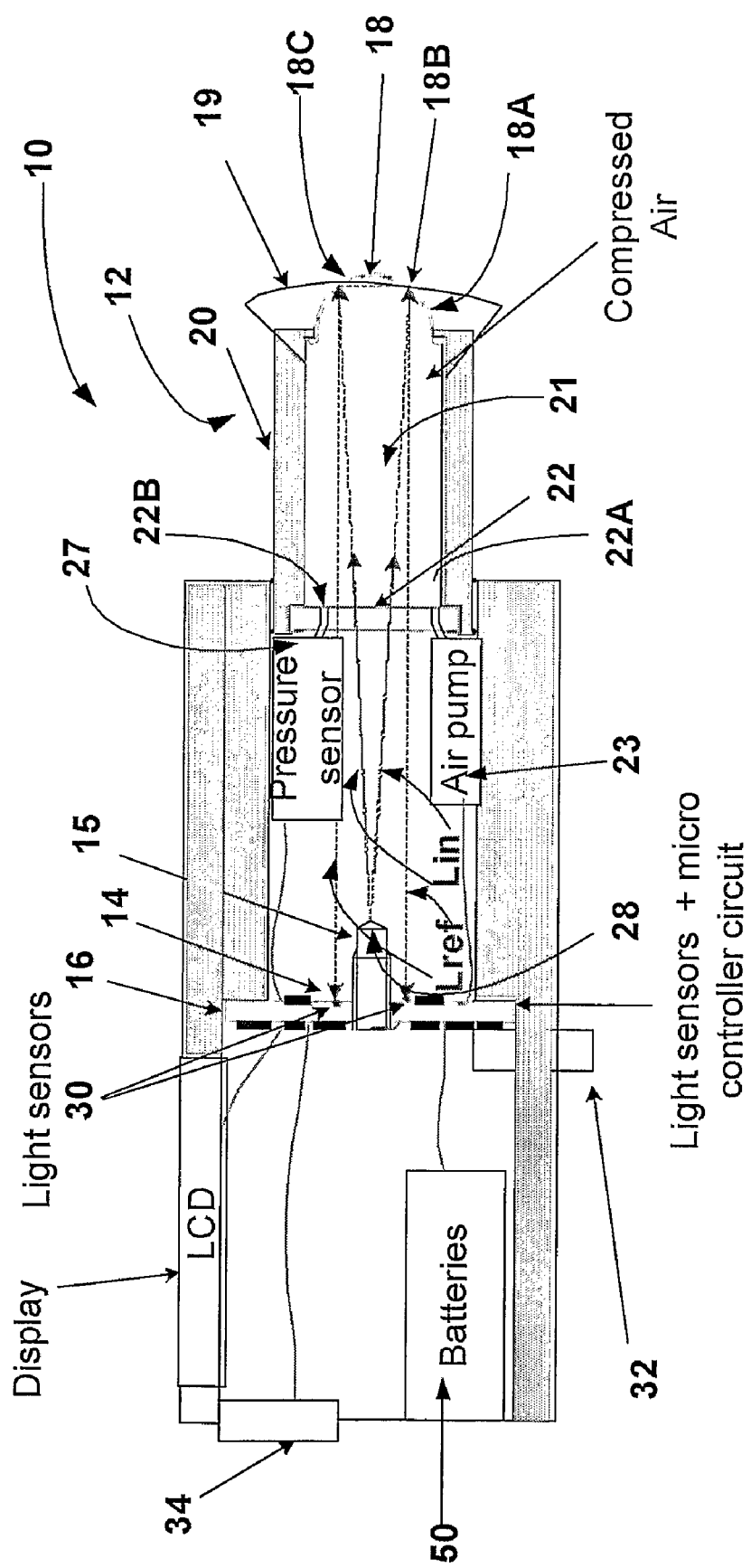
FIG. 2A schematically illustrates an example of the configuration of the device according to the invention.
Figure 2B:
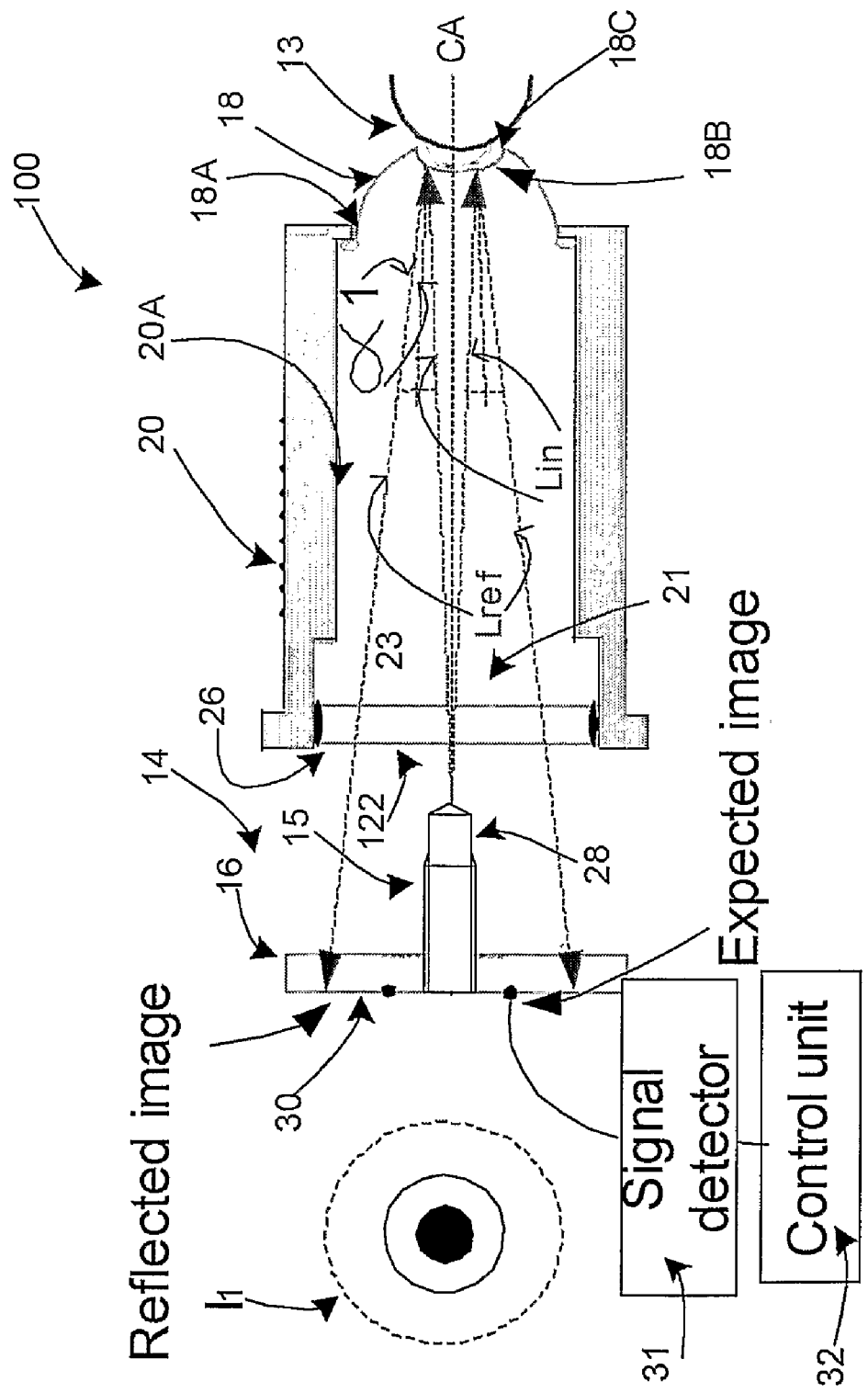
FIGS. 2B and 2C schematically illustrate a device configuration according to another example of the present invention in its two operative positions.
Figure 2C:
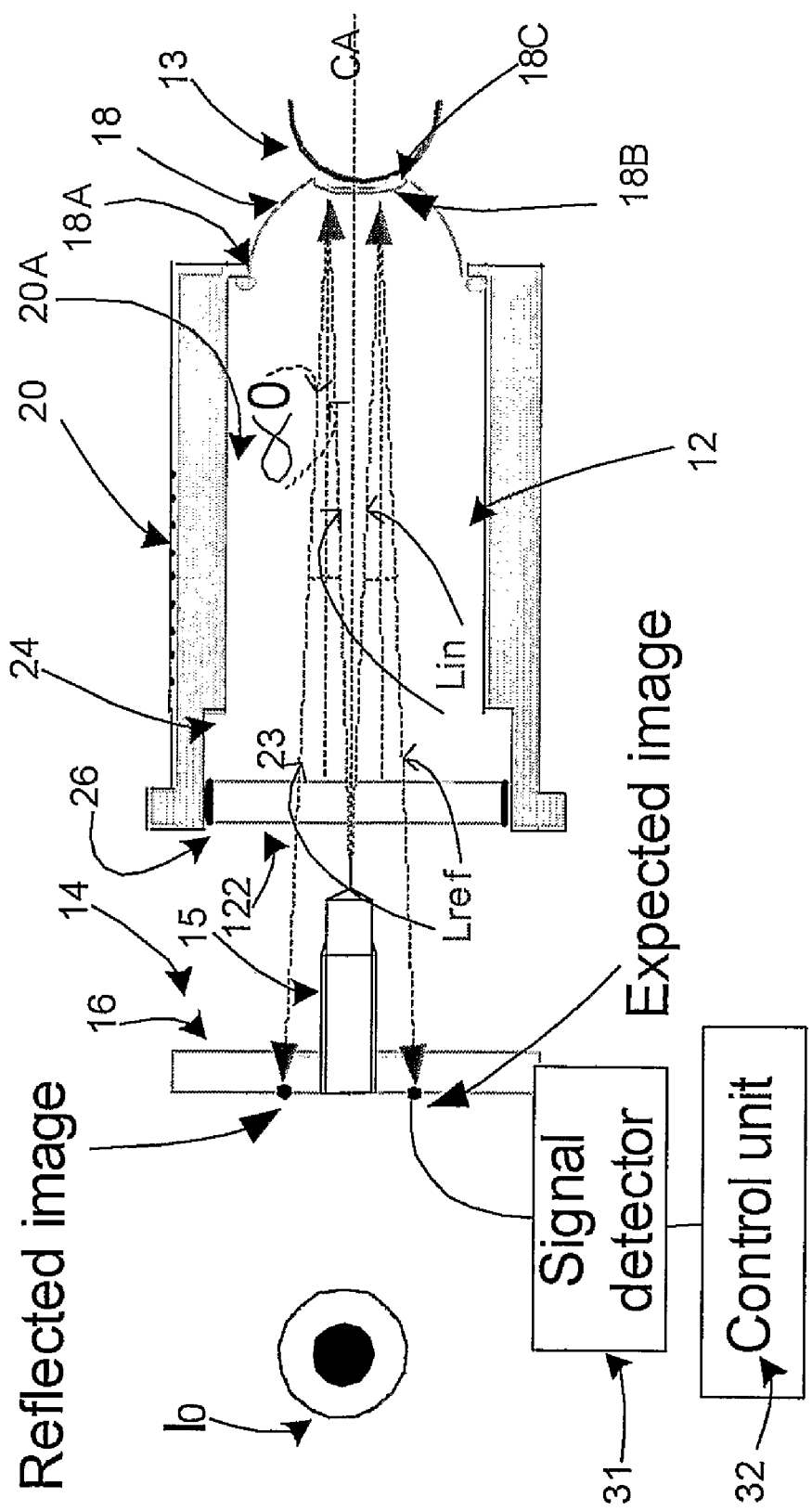

Reference is made to FIGS. 2A to 2C schematically illustrating some specific but not limiting examples of the invention. To facilitate understanding, the same reference numbers are used for identifying components that are common in all the examples of the invention. In the examples described below the reflective membrane (at least its inner surface, and at least within a contacting region of the membrane) is considered, but it should be understood that a fluorescent surface can be used as well, and/or patterned membrane; and/or imaging of an external pattern via the light returned from the membrane.

Device 10 shown in FIG. 2A includes a probe unit 12, which carries a flexible membrane 18 at its distal end, by which it is brought into contact with the patient's eyelid 13, thus enabling deformation of a contacting region 18C of the membrane to match the shape of an eyelid defined by the shape of the cornea. The flexible membrane 18 in its inoperative position (as shown in the figure) has a substantially semi-spherical shape. An inner surface 18B of the membrane 18, at least within the contacting region 18C, is at least partially reflective with respect to a certain light spectrum and may for example be formed with a certain pattern (grid). When the membrane is brought into contact with the eyelid and a force (pressure) is applied to the membrane from the inner side thereof against the eyelid, the contacting region of the membrane deforms to match the eyeball and further to become substantially planar, as will be described below. Deformation of the membrane 18 affects the propagation of light reflected from the reflective surface 18B of the membrane, and if the membrane is patterned the membrane deformation or focusing changes also affects the pattern image. This enables identification of a condition of applanation of a desired area of the membrane, by means of detecting a desired light reflection from the reflective region and/or desired image of the pattern, thus allowing the IOP measurement upon identifying this condition.

Further provided in the device 10 is an optical system 14 including an illuminator unit 15 and a light detection unit 16. The illuminator unit 15 is configured and operable to generate incident light $L_{in}$ of a certain spectrum and direct it towards the inner surface 18B of the contacting region 18C of the membrane 18. Preferably, the illuminator is configured to illuminate at least one substantially circular spot on the membrane. For example, the illuminator may be configured to project a pattern onto the membrane, e.g. an array of at least two concentric rings. The detector unit 16 is configured to receive light $L_{ref}$ reflected from the illuminated region (spot).

The probe 12 has an elongated housing 20 in the form of a hollow cylinder (which in the present example has a varying diameter, implemented by a two-part design of the housing) defining a space for light propagation towards and away from the membrane 18. The membrane 18 is by its periphery region 18A (edge) coupled to the distal end of the housing 20, and when in its inoperative position has a substantially semi-spherical shape. The inner surface 20A of the cylinder 20 is preferably non-reflective with respect to the light spectrum used in the device. To this end, an appropriate anti-reflective coating is applied to the inner surface of the cylinder 20. Preferably, the housing at its distal end is formed with a placer 19 that fixes the device on the eyelid. To this end, external sterile disposable coatings could be used.

The device 10 includes a pressurizing assembly 21 configured and operable (by a control system, e.g. being the utility of the same control unit associated with the optical system) to controllably apply pressure to the membrane 18 against the eyelid, to thereby cause a corresponding force applied from the eyelid side onto the membrane, thus causing deformation of the membrane within the contacting region 18C thereof. In the present example, the pressurizing assembly 21 is as an airpump-based assembly, and includes a transparent sealed element 22 (partition) spaced from the distal end of the housing 20, and formed with an air inlet 22A associated with an air pump 23 and an air outlet 22B associated with a pressure sensor 27. When the device is put in operation, i.e. the membrane is brought into contact with the eyelid, air is pumped into the space between element 22 and membrane 18, the membrane is pressed against the eyelid and is thus deformed under the corresponding force applied from the eyelid, causing the air flow through the outlet, which is indicative of the applied force.

The illuminator unit 15 includes one or more light emitting elements and possibly light directing assembly (fiber) and as indicated above may include a pattern generator (grid), and operates to generate light of the certain spectrum and preferably also of a certain pattern, and direct it onto the membrane, at least onto the contacting region 18C (which is a central region of the membrane). Preferably, the configuration is such that incident light $L_{in}$ propagates along an optical path in the vicinity of the central axis CA of the cylinder 20, and light $L_{ref}$ reflected from the illuminated region of the membrane 18 is collected along a ring-like region surrounding the axis CA. This can be implemented by locating a lighting element 28 (constituted by a light emitter or the distal end of an optical fiber) of the illuminator 15 on the central axis CA of the cylinder 20, and locating one or more annular detecting elements 30 (light sensitive surface or an appropriate optical fiber associated with such surface) of the detector unit 16 so as to surround the lighting element 28.

Preferably, the optical system is configured such that a light detecting element of the detector unit 16 is oriented perpendicular to the central axis CA of the housing 20 and is formed with a central opening coinciding with the central axis, and surrounded by a light sensitive surface 30. The lighting element 28 of the illuminator 14 is placed in this central opening.

In the present example, several concentric annular detectors are used. The desired reflection from the membrane or desired image of the membrane (indicative of the desired applanation of the membrane) is identified as the light detection by a predetermined one of the detectors, or as the detection of maximal light intensity at the predetermined detector, or detection by all the detectors of a predetermined light pattern.

The device operation is controlled by a power source (batteries) 50 and a control unit 32. The latter includes inter alia a microcontroller (data processing and analyzing utilities) 33 associated with the light detectors and the pressurizing assembly, and also a memory utility for storing certain reference data indicative of the desired light response and/or desired image corresponding to the desired applanation of the membrane and its relation to the applied force. The device 10 also preferably includes a control panel 34 and a data presentation utility (e.g., display) 35. During the application of pressure to the membrane against the eyelid, the applied pressure and the detected light are controlled. Upon detecting a condition of the desired applanation of the membrane (applanation of a desired area of the membrane) by detecting the predetermined light reflection condition, a corresponding value of the applied force is measured and used for calculating the IOP.

Preferably, multiple measurement sessions (cycles) are carried out, controlled by on-board CPU (control unit 32), and measurement results are displayed. The results can be stored and/or transmitted (e.g., via a communication network) to a physician. The multiplicity of measurements may be then averaged. The control unit may be preprogrammed in accordance with the patient's peculiarities. The control unit may be configured as the so-called "expert system" for learning the patient's peculiarities.

Thus, the device provides for measuring the force applied onto the membrane from the eyelid, which force when corresponding to the desired applanation of the membrane is indicative of the IOP. On the other hand, the device provides for detecting the desired applanation of the membrane due to the detection of the desired light reflection from the membrane. Generally speaking, the device is configured to enable measurements of a force applied to the membrane from the eyelid, and identification of a condition of the desired light detection from the membrane (i.e., desired applanation of the membrane) while being pressed against the eyelid. In the present specific but not limiting example, the force measurements are based on the use of an airpump-based assembly, and the identification of the desired reflection is based on the use of several light detecting elements. When light is reflected from the planar and curved membrane, reflected light components propagate from the membrane along different optical paths, respectively, and accordingly impinges onto different detectors, which can easily be identified FIGS. 2B and 2C illustrate another example of a device 100 in its two operative positions. To facilitate understanding, the same reference numbers are used for identifying components that are common in all the examples of the invention. When in an operative position of the device, i.e., when the membrane 18 is brought into contact with the eyelid, the membrane 18 is deformable from a curved position of the contacting region 18C matching the eyeball shape (FIG. 2B) into a substantially planar position of the contacting region 18C (FIG. 2C), under application of force against the eyelid.

In the present example, a pressurizing assembly 121 includes a piston 122 transparent to a light spectrum used in the device 100 and a substantially non-compressible light transparent liquid medium 23 (such as liquid silicon gel) that fills a space between the piston 122 and the membrane 18. The piston 122 is driven by an appropriate driving assembly as will be described further below, for reciprocating movement along the longitudinal axis CA of the housing. Pressure (force) applied to the piston 122 causes the application of force (proportional to the applied pressure) onto the external surface of the membrane 18 within the contacting region 18C, when the membrane is brought into contact with the eyelid.

Preferably, the housing 20 is configured so as to appropriately restrict the piston movement (i.e., define the maximal distance of the piston movement), and thus prevent the applied force to exceed a certain value. In the present example, this is implemented by configuring the inner surface 22A of the housing 20 to define a protrusion 24 and a rubber seal 26 spaced from the protrusion 24 a certain distance d. Hence, the piston 122 can move towards and away from the distal end of the housing only within the distance d. It should, however, be understood that the present invention is not limited to this specific example, and other configurations of a pressurizing assembly, as well as other movement restriction means, if needed, could be used, for example a spring of a desirably limited tension which thus also constitutes a safety overpressure protection mechanism.

As indicated above, the device includes an identification arrangement enabling identification of the condition of pre-determined (desired) detection of light returned from the illuminated membrane, and accordingly of the applanation of the desired area of the membrane as a result of a force (pressure) applied from the eyelid side. In the present example, such identification arrangement is implemented by providing the light sensitive surface 30 of a detector unit with a reference mark RM in the form of a ring of a certain diameter $D_o$ around the central opening (i.e., around the incident light propagation path) and optionally a signal generator 31 connected to the output of the detector. This reference mark RM (ring of diameter $D_0$) is indicative of an expected "image" $I_0$ of the illuminated membrane region corresponding to the desirably flattened membrane 18.

FIG. 2B shows the slightly pressed membrane 18, when the central portion 18C of the membrane 18 is deformed due to the force applied from the eye to cause the membrane portion 18C to match the eyeball shape. Incident light $L_{in}$ impinges on such a curved membrane portion 18C and is reflected there-from at angle $\alpha_1$; reflected light $L^{(1)}_{ref}$ propagates along a respective optical path through the housing 20 and creates on the detecting surface 30 an image $I_1$ in the form of a ring of a diameter $D_1$ larger than the expected one. As shown in FIG. 2C, when the contacting region 18C of the membrane becomes desirably flattened, light impinges on the membrane region 18C and is reflected therefrom at a different angle $\alpha_0$ resulting in the desired reference image $I_0$.

Generally, light received by the detecting surface 30 within the reference mark region RM can be visually identified by a physician or operator, who can thus activate a control unit 32 (processor) to calculate the applied force corresponding to such an applanated condition of the desired area of the membrane, and hence calculate the respective IOP value. Preferably, an electronic identification and indication arrangement is used: data (detector output) indicative of the desired image (detection of the desired light reflection) is received at the control unit 32 (chip) which actuates generation of an indication signal, e.g., acoustic signal. Alternatively, the same can be implemented by connecting the electrical output of the reference mark RM region of the detecting surface 30 to an acoustic unit 31 (signal generator). Thus, the device provides an output indicating signal actuating the IOP calculation only when the desired image $I_0$ is created.

It should be understood that detection of the desired reflection can be identified by a desired pattern of the detected light (image) as described above, as well as by predetermined intensity of the detected light. It should also be understood that, generally, the optical system can be configured to direct incident and reflected light along different optical paths, i.e., direct incident light along an axis tilted with respect to the central axis CA of the housing. Also, the reflective surface 18B of the membrane may be in the form of a continuous reflective coating or a certain pattern of reflective regions (an array of spaced-apart non-reflective and reflective regions). The reflective surface may and may not be mirror-like; the reflective surface may be in the form of regions of different colors. It should also be noted that the optical system may include an optical mask located in an optical path of light coming from the reflective membrane, such that deformation of the membrane affects an image of the mask on the detector. Additionally, detection of the desired reflection from membrane (i.e., desired applanation of membrane) can be identified by locating the light sensitive surface only where the desired image is to be created, such that as long as the membrane is not desirably flattened, reflected light propagates outside the light detecting surface, and thus detection of reflected light occurs only when the membrane is desirably flattened. It should also be noted that several measurements can be taken corresponding to different flattened areas of the membrane, thus allowing for averaging the results, and obtaining patient specific parameters, to thereby allow calibration of the results per patient and thus provide better accuracy. Additionally, the device may be configured and operable for projecting one or more different light patterns on the membrane surface, rather than a circular spot.

Reference is made to FIGS. 3A-3D illustrating more specifically the configuration and operation of probe 12. In the present example, the pressurizing assembly of FIGS. 2B-2C is used, but it should be understood that the principles of the membrane deformation for the IOP measurement can be realized using any other suitable assembly, for example that of FIG. 1.

Figure 3A:
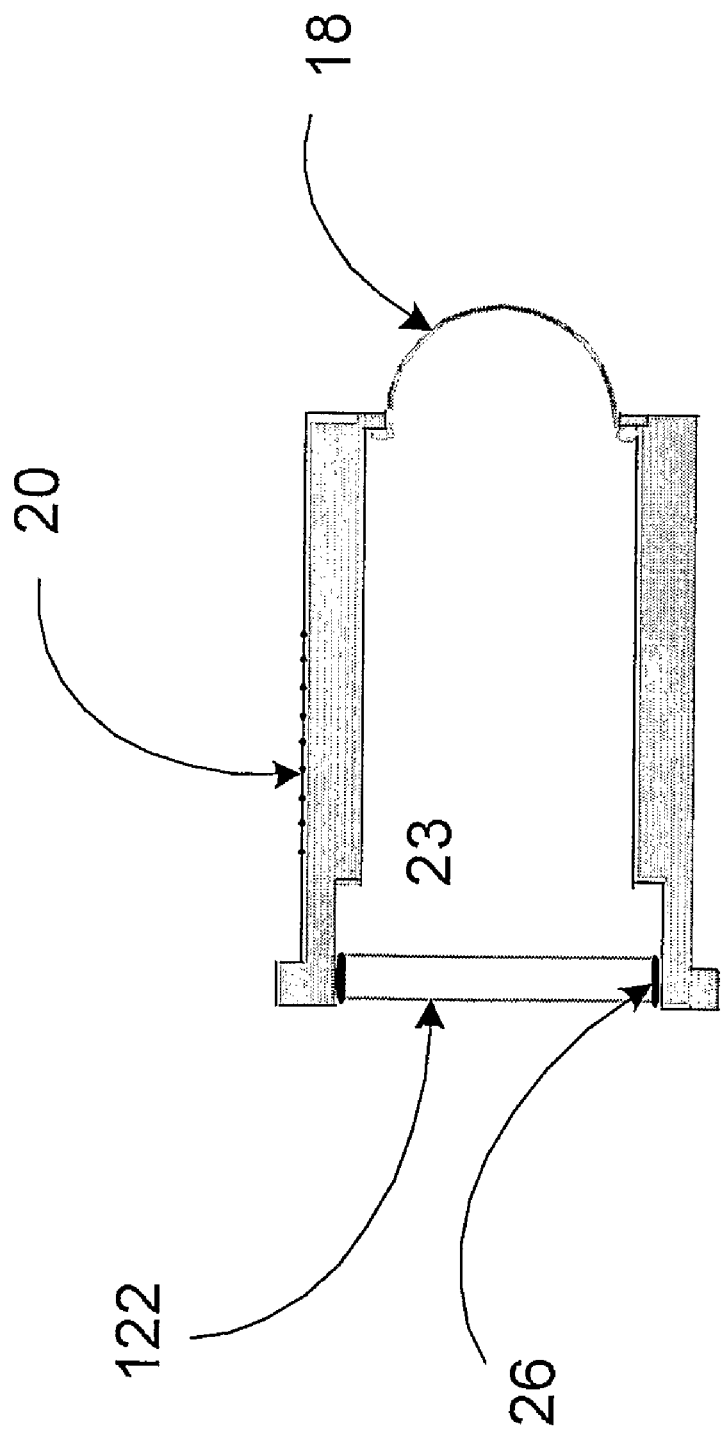
Figure 3B:
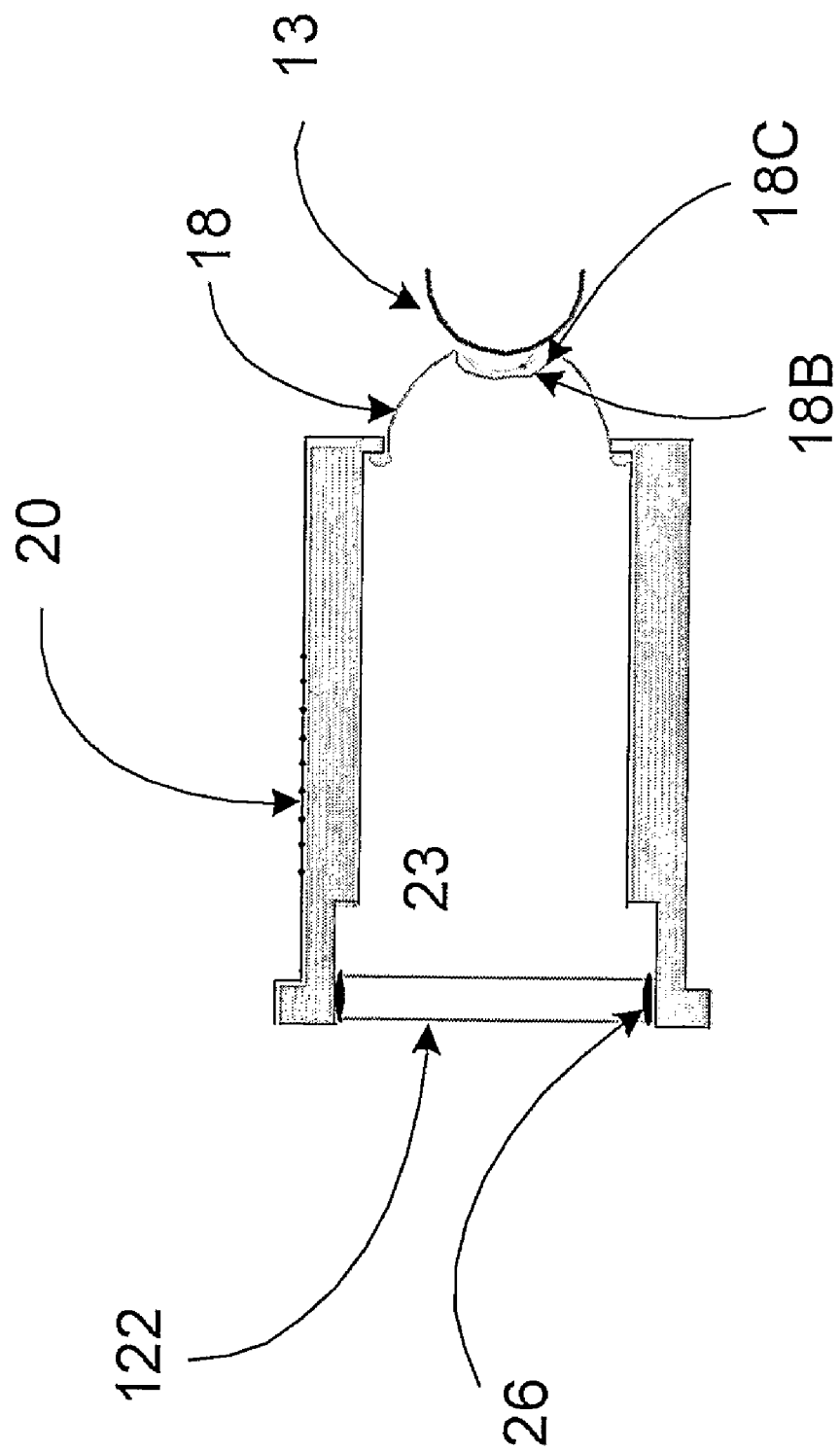

FIG. 3A shows an inoperative position of the probe, when the membrane 18 is in its inoperative position, having a dome-like (substantially semi-spherical) shape. As shown in FIG. 3B, when the membrane is brought into contact with the eyelid 13, it presses on the eyelid 13, and the region 18C of membrane contacting the eyelid deforms to match the shape of the eyeball, mainly the cornea. When force/pressure is applied to the membrane, i.e., the piston 122 moves towards the distal end of the housing, this pressure is transmitted to the membrane 18 through the liquid medium 23, and the membrane region 18C gradually undergoes applanation from the center thereof: the membrane center equalizes forces with the eye, and thus a certain area $A_1$ of the membrane is applanated (FIG. 3C). A required applanation is shown in FIG. 3D: applanated area $A_0$ reaches a required size, hence equalized force with eye is indicative of the internal eye pressure.

Turning back to FIGS. 2B and 2C, the desired flattened area $A_0$ of the membrane is determined by the specific diameter of the image, i.e., the diameter $D_0$ of the reference mark ring RM. The lighting element (e.g., laser) 28 illuminates a required spot-size S on the inner surface 18B of the membrane within the central region 18C thereof. As long as the spot S is illuminated on the non-planar surface of the membrane (FIG. 2B), the reflected light arrives on the detecting surface 30 within a ring of diameter $D_1$ larger than that provided by light reflection of the desirably planar surface of the membrane 18C (FIG. 2C). Practically, the diameter $D_0$ of the detected ring resulted from the desirably planar surface is slightly larger than that of the illuminated spot S. When the membrane reaches the desired applanation, the detected image matches the reference one, which can be detected visually (which is sufficient in the case the measurement is carried out by a physician or operator) and/or electronically using an appropriate electronic circuit (chip), e.g., utilizing acoustic means, or fully automatically as described above with reference to FIG. 2A. The indication signal (or the operator/physician) operates the processor (control unit) 32 which is preprogrammed to be responsive to the indication signal to calculate the IOP value from the corresponding force value, considering that the respective membrane area $A_0$ is previously calibrated and is thus known.

Figure 4:
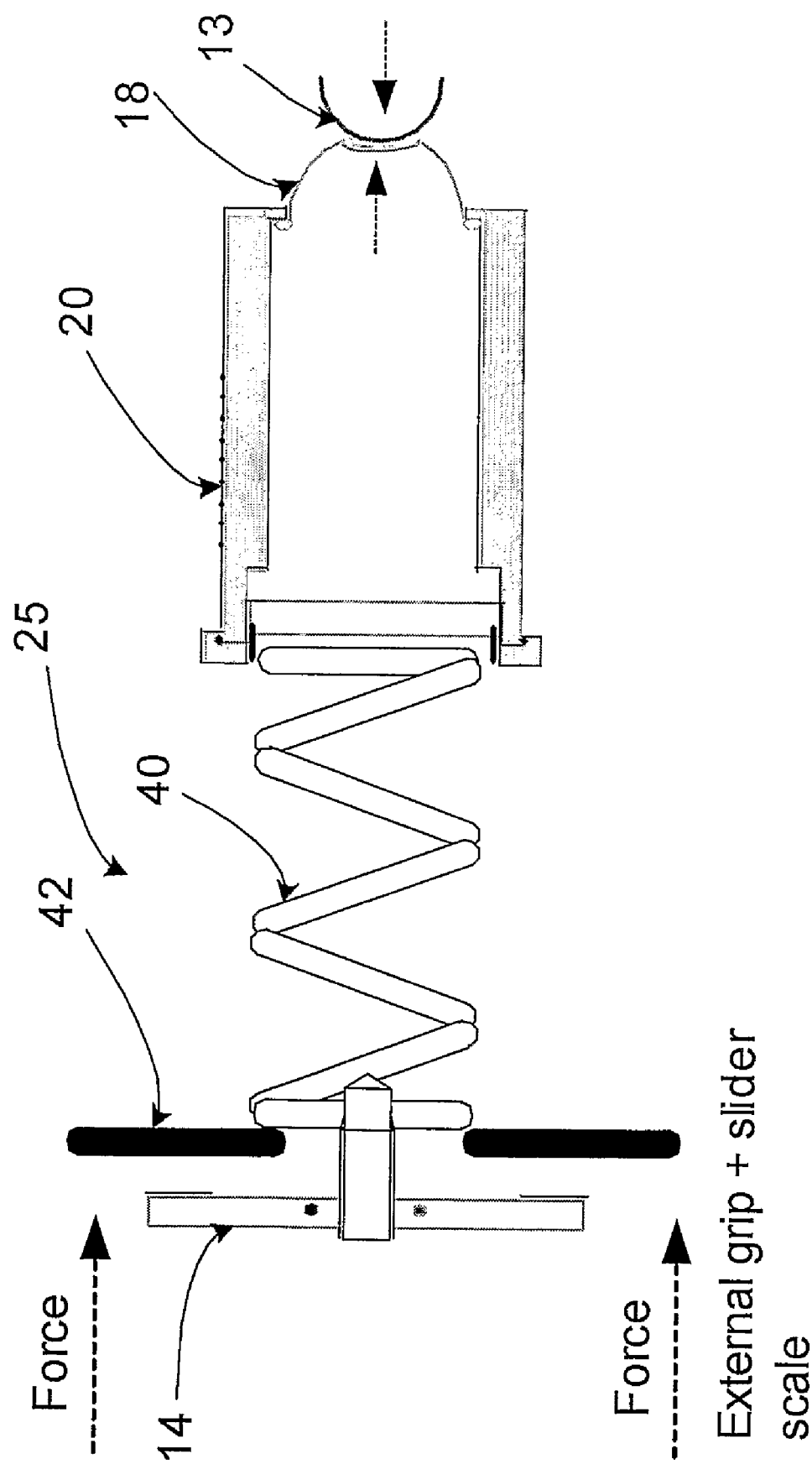
FIG. 4 is a schematic illustration of an example of a drive assembly suitable to be used in the device of FIGS. 2A-2D to apply pressure to the membrane against a patient's eyelid.

Reference is made to FIG. 4 exemplifying a piston driving assembly 25 suitable to be used in the device 100. The drive assembly 25 includes a helical spring 40 which is by its one end connected to a pin (handle) 42. The latter can be pushed either manually or by a suitable electrical motor (e.g., stepper) which is not specifically shown. The other end of the spring 40 is brought into contact with the piston 122. The use of a helical spring allows for the light passage therethrough between the membrane and the optical system. It should, however, be understood that the invention is not limited to this specific example. The device can be configured such that the piston driving assembly is located outside the optical paths of incident and reflected light. The spring 40 has a known spring constant (ratio of load to deflection of the spring), and the spring contraction is indicative of the applied pressure (force). This information can be obtained using various techniques, for example by using an external grip movable on the pre-calibrated slider scale.

Generation of a warning or indication signal (e.g., acoustic signal) for measuring the IOP while preventing the application of extra force can be based on defining the minimal spring length (i.e., maximal force), where a simple electric contact actuates the acoustic signal generation. Since the force F is determined as $F=Kx$, whereas x is the length of the spring, a certain value of x designates a certain applied force F, therefore a minimal contracted spring length $x_{min}$ can be set as a limit for the maximal applied force $F_{max}$. Additionally, a mechanical mechanism can be used for the same purpose, such that when a certain force is exceeded the application of force is halted due to the disconnection between the handle 42 and the spring 40.

Figure 5:
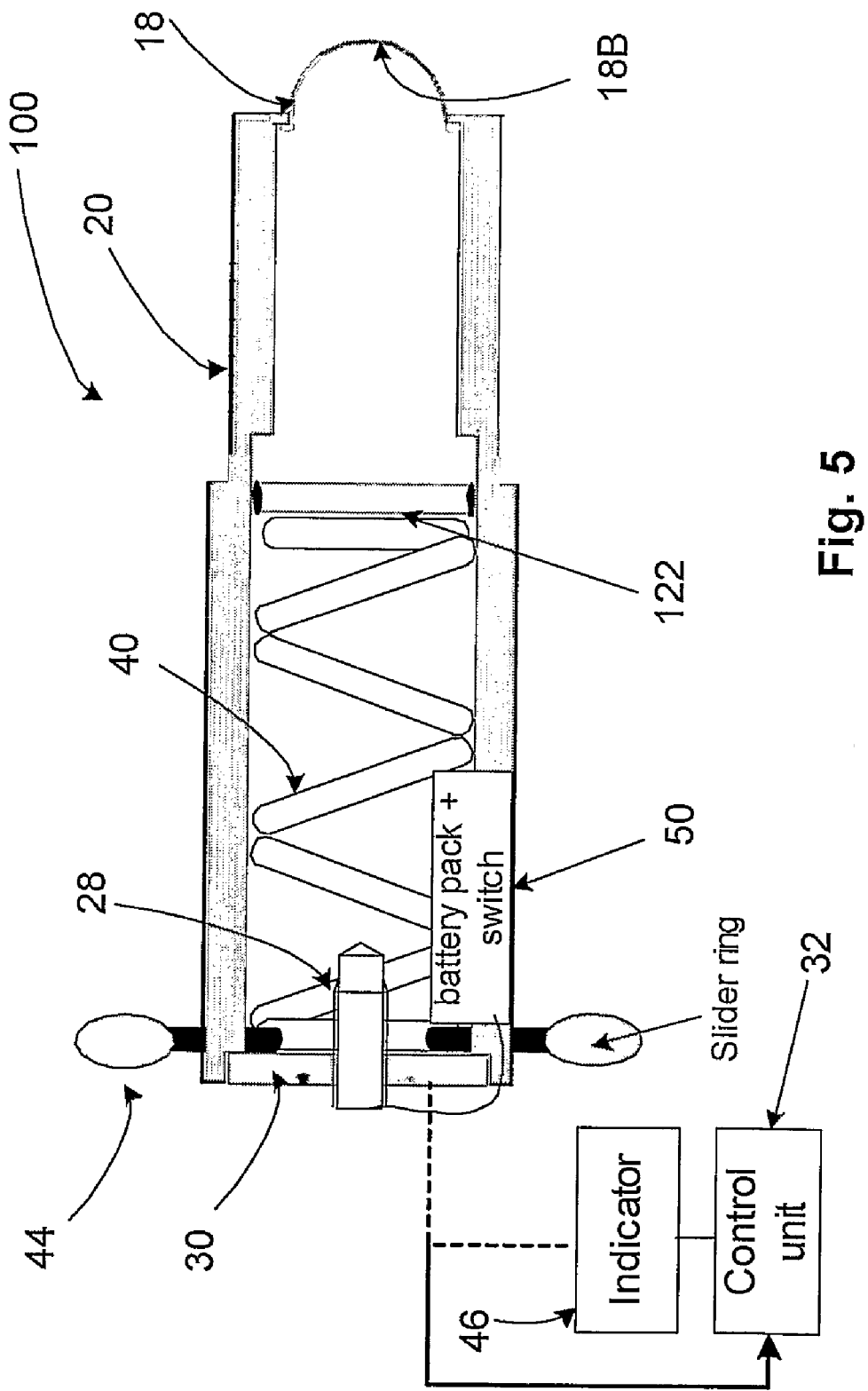
FIG. 5 more specifically illustrates the configuration of the device of FIGS. 2B-2C.

Referring to FIG. 5, there is illustrated more specifically the configuration of device 100 utilizing the above-described designs of the probe 12 and drive assembly 25. The device 100 thus includes a probe 12; an optical system 14 (illuminator unit 15 and a light detector unit 16); a control unit 32 (e.g., including an indicator and a processor); and a power supply unit 50. The probe 12 is configured and operable as described above, namely includes a flexible membrane 18 located at the distal end of a hollow cylindrical housing 20 and having at least partially reflective inner surface 18B at least within a contacting region 18C thereof, and a transparent piston 122 kept by rubber seal and spaced from membrane 18 by substantially non-compressible liquid medium 23 and driven for reciprocating movement by a helical spring based drive assembly 25. The illuminator 15 includes a lighting element (laser module) 28 producing a substantially circular spot on the reflective surface 18B within the central region 18C of membrane 18. The detector unit 16 includes a light sensitive element 30 having a central opening carrying the laser module and light sensitive surface surrounding the laser module 28. A slider ring on scale 44 is used for measuring the pressure/force applied to the piston. The power supply unit 50 is a battery pack with switch coupled to the respective elements of the device in a conventional manner. The slider ring assembly 44 (constituting a pressure measurement unit) is connected to the control unit 32. The latter is also connectable to the output of the detector 16 or output of an indicator arrangement 46 to carry out calculation of the IOP in response to the indication signal and based on the measured pressure applied to the piston. The indicator arrangement 46 includes a signal generator (e.g., acoustic unit) responsive to data (electrical output of the detector) indicative of the detection of the desired light reflection.

The device of the present invention can utilize simple, available in the market and non-expensive components; is easy to operate, and provides for accurate measurement of IOP, which does not require the physician involvement in the measuring procedure, and is harmless and painless for patients.

Those skilled in the art to which the present invention pertains can appreciate that while the present invention has been described in terms of preferred embodiments, the concept upon which this disclosure is based may readily be utilized as a basis for other designs of the device of the present invention. Also, it is to be understood that the phraseology and terminology employed herein are for the purpose of description and should not be regarded as limiting. It is important, therefore, that the scope of the invention is not construed as being limited by the illustrative embodiments set forth herein. Other variations are possible within the scope of the present invention as defined in the appended claims and their equivalents.

The invention claimed is:

1. A device for use in non-invasive measurement of a patient's intra-ocular pressure (IOP), the device comprising:
   a probe unit having a flexible membrane which is to be brought into contact with
   a patient's eyelid when the device is put in operation enabling a non-invasive measurement of a patient's intra-ocular pressure (IOP), wherein
   at least a contacting region of the membrane is deformable, by applied force, between a first curved shape thereof matching a geometry of an external surface of the eyelid defined by the shape of the patient's cornea and a second shape corresponding to a condition of applanation of a desired area of the contacting region, said desired area being of a size corresponding to desirable deformation of a specific area of the cornea;

said flexible membrane has an inner surface at said contacting region responding to incident light by reflection and/or fluorescence, to reflect or emit a light image pattern, wherein a change in the condition of applanation of the desired area of the contacting region causes a change in said light image pattern;

deformation of the membrane, while being illuminated by incident light and when the force is applied to the membrane against the eyelid, results in the change in condition of applanation effecting a change in the light image pattern from the membrane;

an optical system configured for directing illuminating light towards said inner surface of the contacting region of the membrane, detecting said light image pattern from the illuminated membrane region, and generating data indicative of the detected light image pattern, and, a control unit connectable to the output of the optical system and configured to apply signal processing to the output data for analyzing said data indicative of the detected light image pattern to detect when said detected light image pattern corresponds to a reference pattern to identify the applanation area of the contacting region of the membrane and therefore of a flattened surface area of the cornea allowing the IOP measurement upon identifying said area;

the probe being configured to enable controllably varying application of the force to the membrane against the eyelid.

2. The device of claim 1, wherein an inner surface of the membrane, at least within the contacting region, is at least partially reflective.

3. The device of claim 1, wherein the probe has a hollow housing defining a space for light propagation towards and away from the membrane attached to the distal end of the housing.

4. The device of claim 3, wherein an inner surface of the housing is substantially non-reflective with respect to the illuminating light and light returned from the membrane.

5. The device of claim 1, wherein the optical system is configured for projecting a certain pattern or image onto the membrane, detected light indicative of said pattern or image enabling identification of an area of applanation of said contacting region.

6. The device of claim 1, wherein the optical system is configured for passing the light returned from the membrane through a certain pattern, detected image of said pattern being indicative of an area of applanation of said contacting region.

7. The device of claim 1, wherein the optical system comprises an illuminator unit for generating light of a certain spectrum and directing it onto said region of the membrane, and a light detection unit configured for detecting the light returned from the illuminated region and generating data indicative thereof.

8. The device of claim 7, wherein said light detection unit is configured to generate data indicative of the detection of a predetermined light reflection of the membrane.

9. The device of claim 8, wherein said light detection unit comprises a light sensitive surface having a reference mark defining the detection of the predetermined light reflection from the illuminated region of the membrane.

10. The device of claim 8, wherein said light detection unit comprises a light sensitive element positioned in an optical path of light reflected from the membrane, such that the light reflection from the membrane when at an area other than said area of applanation propagates outside said optical path.

11. The device of claim 8, wherein the light sensitive element is configured to surround an optical path of the incident light propagation.

12. The device of claim 7, wherein the optical system is configured as an imaging system.

13. The device of claim 12, wherein the illuminator unit comprises a pattern generator for projecting the pattern onto the membrane.

14. The device of claim 7, wherein the illuminator unit comprises a lighting element accommodated at a central axis of a hollow housing, which carries said membrane at its distal end, the lighting element being configured and operable to illuminate on the reflective inner surface of the contacting region of the membrane a certain illuminated pattern; and the light detection unit is configured to define a light sensitive element surrounding the lighting element.

15. The device of claim 14, wherein said light detection unit comprises a light sensitive surface having a reference mark defining the detection of the desired light reflection from the illuminated region of the membrane, said reference mark being in the form of an annular region of the light sensitive element around the lighting element.

16. The device of claim 7, comprising a control unit connectable to the output of the detection unit and configured to apply signal processing to the output data for analyzing the data indicative of the detected light and identifying the applanation area.

17. The device of claim 1, wherein said probe comprises a pressurizing assembly configured and operable to apply pressure to an inner surface of the membrane, to thereby cause the application of force against the eyelid when the membrane is brought into contact with the eyelid.

18. The device of claim 17, wherein the pressurizing assembly comprises an air pump assembly configured to apply air pressure to the membrane.

19. The device of claim 18, wherein the pressurizing assembly comprises an optically transparent sealed partition spaced from the distal end of the probe, said partition having an air inlet associated with an air pump operable to supply air into said space and an air outlet associated with a pressure sensor for measuring the force applied from the eyelid to the external surface of the membrane when being pressed by the air.

20. The device of claim 1, comprising a motion control or force applying mechanism for driving the probe for a reciprocating movement towards and away from the eyelid.

21. The device of claim 20, wherein said motion control mechanism comprises a spring operated to apply pressure to the probe to move said probe in a direction towards the membrane.

22. The device of claim 1 comprising an indication arrangement configured to generate an indication signal upon detecting the condition of applanation of the desired area of the membrane to thereby actuate calculation of the respective IOP value.

23. The device of claim 1 comprising a measurement unit for measuring pressure applied to the membrane from the inner side thereof.

24. The device of claim 17, comprising a measurement unit for measuring pressure applied to the membrane by said pressurizing assembly.

25. The device of claim 24, comprising an indication arrangement configured to generate an indication signal upon detecting the condition of applanation of the desired area of the membrane to thereby actuate calculation of the respective IOP value; wherein the indication arrangement comprises a signal generator responsive to data indicative of the detection of the desired light response, an output of the signal generator being connectable to a control unit preprogrammed to be responsive to the indication signal and to the measured pressure to calculate the corresponding IOP value.

26. The device of claim 1, comprising a control system configured and operable to actuate more than one measurement session, different measurement sessions being controlled to detect different conditions of the membrane applanation under the application of force against the eyelid; and to average measurement results.

27. A device according to claim 1, wherein said desired area is of such size that the force required for applanation of a contacting region of the desired area is indicative of the IOP.

28. A device for use in non-invasive measurement of a patient's intra-ocular pressure (IOP), the device comprising:
  a probe unit having a flexible membrane which is to be brought into contact with a patient's eyelid when the device is put in operation enabling a non-invasive measurement of a patient's intra-ocular pressure (IOP), wherein at least a contacting region of the membrane is deformable, by applied force, between a first curved shape thereof matching a geometry of an external surface of the eyelid defined by the shape of the patient's cornea and a second shape corresponding to a condition of applanation of a desired area of the contacting region, said desired area being of a size corresponding to desirable deformation of a specific area of the cornea said flexible membrane has an inner surface at said contacting region responding to incident light by reflection and/or fluorescence, to reflect or emit a light image pattern, wherein a change in the condition of applanation of the desired area of the contacting region causes a change in said light image pattern;
  deformation of the membrane, while being illuminated by incident light and when the force is applied to the membrane against the eyelid, results in the change in condition of applanation effecting a change in the light image pattern from the membrane; and,
  an optical system configured for directing illuminating light towards said inner surface of the contacting region of the membrane, detecting said light image pattern from the illuminated membrane region, and generating data indicative of the detected light image pattern, thereby enabling identification of a condition of applanation of a desired area of the contacting region of the membrane by detecting when said detected light image pattern corresponds to a reference pattern and therefore identifying a flattened surface area of the cornea allowing the IOP measurement upon identifying said area;
  the probe being configured to enable controllably varying application of force to the membrane against the eyelid, wherein said probe comprises a pressurizing assembly configured and operable to apply pressure to an inner surface of the membrane, to thereby cause the application of force against the eyelid when the membrane is brought into contact with the eyelid, wherein the pressurizing assembly comprises an air pump assembly configured to apply air pressure to the membrane.

29. The device of claim 28, wherein, said piston is driven for the reciprocating movement by a motion control mechanism.

30. The device of claim 29, wherein said motion control mechanism comprises a spring located outside said space and operated to apply pressure to said piston to move said piston in a direction towards the membrane.

31. The device of claim 30, wherein said optical system and the helical spring are accommodated such that the illuminating and returned light pass through said helical spring.

32. The device of claim 29, configured to restrict the movement of the piston to a certain distance to thereby prevent the applied force to exceed a predetermined value.

33. A device for use in non-invasive measurement of a patient's intra-ocular pressure (IOP), the device comprising:
  a probe unit having a flexible membrane which is to be brought into contact with a, patient's eyelid when the device is put in operation enabling a non-invasive measurement of a patient's intra-ocular pressure (IOP),
  wherein at least a contacting region of the membrane is deformable, by applied force, between a first curved shape thereof matching a geometry of an external surface of the eyelid defined by the shape of the patient's cornea and a second shape corresponding to a condition of applanation of a desired area of the contacting region, said desired area being of a size corresponding to desirable deformation of a specific area of the cornea; the flexible membrane has an inner surface at said contacting region responding to incident light by reflection and/or fluorescence, to reflect or emit a light image pattern, wherein a change in the condition of applanation of the desired area of the contacting region causes a change in said light image pattern;
  deformation of the membrane, while being illuminated by incident light and when the force is applied to the membrane against the eyelid, results in the change in condition of applanation effecting a change in the light image pattern from the membrane; and
  an optical system configured for directing illuminating light towards said inner surface of the contacting region of the membrane, detecting said light image pattern from the illuminated membrane region, and generating data indicative of the detected light image pattern, thereby enabling identification of a condition of applanation of a desired area of the contacting region of the membrane when the detected light image pattern corresponds to a reference pattern and therefore identifies a flattened surface area of the cornea allowing the IOP measurement upon identifying said area;
  the probe being configured to enable controllably varying application of force to the membrane against the eyelid, wherein said probe comprises a pressurizing assembly configured and operable to apply pressure to an inner surface of the membrane, to thereby cause the application of force against the eyelid when the membrane is brought into contact with the eyelid, wherein the probe has a hollow housing defining a space for light propagation towards and away from the membrane attached to the distal end of the housing, the pressurizing assembly comprising an air pump assembly configured to apply air pressure to the membrane.

34. The device of claim 33, wherein said piston is driven for the reciprocating movement by a motion control mechanism.

35. The device of claim 34, wherein said motion control, mechanism comprises a spring located outside said space and operated to apply pressure to said piston to move said piston in a direction towards the membrane.

36. The device of claim 35, comprising an optical system configured for directing the illuminating light towards the inner surface of the contacting region of the membrane and detecting the light returned therefrom, the optical system and the helical spring being accommodated such that the illuminating and returned light pass through said helical spring.

37. The device of claim 34, wherein the housing is configured to restrict the reciprocating movement of the piston to a certain distance to thereby prevent the applied force to exceed a predetermined value.

38. A method for use in non-invasive measurement of intra-ocular pressure (IOP), the method comprising:
- providing a flexible membrane having a certain light responsive pattern at an inner surface of the membrane,
- bringing the membrane, by an outer surface thereof, in contact with a patient's eyelid,
- applying controllably varying force to the membrane against the eyelid causing deformation of the contacting region of the membrane to match a shape of the eyelid defined by the shape of the patient's cornea, such that further deformation of the membrane causes applanation of the contacting region of the membrane,
- illuminating the membrane and detecting an image of said certain pattern from the illuminated membrane region, the detected image of the certain pattern being indicative of an area of applanation of said contacting region and of a flattened surface area of the cornea;
- identifying a condition of a predetermined deformation of a desired area of the contacting region of the membrane by identifying the change in the pattern enabling identification of condition of applanation of a desired area of said membrane by identifying said pattern in the detected image from the membrane and comparing the identified pattern with a reference pattern to detect when said identified pattern corresponds to said reference pattern and, thereby identify the applanation of said desired area, and
- measuring the IOP upon the identifying.

* * * * *

UNITED STATES PATENT AND TRADEMARK OFFICE
CERTIFICATE OF CORRECTION

| | |
|---|---|
| PATENT NO. | : 8,317,701 B2 |
| APPLICATION NO. | : 11/816449 |
| DATED | : November 27, 2012 |
| INVENTOR(S) | : Livne et al. |

It is certified that error appears in the above-identified patent and that said Letters Patent is hereby corrected as shown below:

In the Claims:

In claim 33, column 16, line 10, please remove the "," after the word "a".

Signed and Sealed this
Sixteenth Day of April, 2013

Teresa Stanek Rea
*Acting Director of the United States Patent and Trademark Office*